USFC Patent [19]

Schuldt, Jr.

[11] 4,135,000
[45] Jan. 16, 1979

[54] PROCESS FOR REDUCING THE RIBONUCLEIC ACID CONTENT OR YEAST PROTEIN

[75] Inventor: Erich H. Schuldt, Jr., St. Louis County, Mo.

[73] Assignee: Anheuser-Busch, Incorporated, St. Louis, Mo.

[21] Appl. No.: 867,305

[22] Filed: Jan. 5, 1978

Related U.S. Application Data

[63] Continuation-in-part of Ser. No. 710,733, Aug. 2, 1976, abandoned.

[51] Int. Cl.$^2$ .............................................. A23J 1/18
[52] U.S. Cl. ...................................... 426/60; 426/62; 426/656; 260/112 R
[58] Field of Search ...................... 426/60, 62, 61, 656; 195/2, 4, 5, 28 N, 28 R, 82, 114; 260/112 R

[56] References Cited

U.S. PATENT DOCUMENTS 3,616,249  10/1971  Cavallo et al. ................ 195/28 R X
3,887,431  6/1975  Robbins et al. ........................ 195/5

OTHER PUBLICATIONS

Nord "Advances in Enzymology" Interscience Publishers 1962, pp. 235-243.

Primary Examiner—R. B. Penland
Attorney, Agent, or Firm—Gravely, Lieder & Woodruff

[57] ABSTRACT

This disclosure relates to a process for producing a yeast protein by treating the yeast medium with zinc at critical points in the process to protect the endogenous nuclease when the pH of the medium is raised during separation of the protein from the cell walls. The endogenous nuclease then is available to reduce the nucleic acid content of the protein during a subsequent incubation step.

The yeast cells are ruptured by homogenization; extracted to remove the protein from the cells; and the cell wall debris separated by centrifugation. The soluble fraction is treated with alkali to enable the endogenous ribonuclease to degrade the nucleic acid. Specifically it has been found that adding zinc to the growing yeast, or to the cells before homogenization, or to the homogenate of cell walls and yeast protein before it is made highly alkaline will permit the endogenous nuclease of the yeast to degrade its own nucleic acid to tolerable levels.

7 Claims, No Drawings

PROCESS FOR REDUCING THE RIBONUCLEIC ACID CONTENT OR YEAST PROTEIN

CROSS REFERENCE TO RELATED APPLICATION

This application is a continuation-in-part of prior co-pending application of Schuldt Ser. No. 710,733 filed Aug. 2, 1976, now abandoned.

BACKGROUND OF THE INVENTION

There has been considerable information published on the production of microbial protein. The term "microbial protein" has developed two meanings. One meaning connotes the whole cell, in which the protein is contained within the confines of the cell wall and therefore is relatively nonfunctional. The other meaning connotes a protein isolated as a separate entity from the microbe. In either case, for human nutrition, the nucleic acid content of the protein product should be reduced to below about 9% by weight, if yeast protein is a substantial source of protein in a human diet. The Recommended Daily Allowance of The Food and Nutrition Board, National Research Council, for protein is 65 grams per day for a 70 kilogram adult male. The Protein Advisory Group of the United Nations System recommends that the amount of nucleic acid ingested per day from microbial protein should be less than 2 grams. Therefore, the nucleic acid content of the protein should be less than 6%, if yeast protein supplies 50% of the dietary protein. The nucleic acid should be below about 3% if yeast is the sole source of protein in the diet.

The nucleic acid content of yeast cells, such as *Candida utilis* and *Saccharomyces cerevisiae*, is about 12 to 15 grams of nucleic acid per 100 grams of crude protein. Crude protein is calculated for purposes of this application as the Nitrogen (Kjeldahl) content multiplied by 6.25. The protein isolated from these cells also contain 12 to 15 grams nucleic acid per 100 grams of crude protein. Thus, the nucleic acid content should be reduced several fold before a substantial amount of the protein is used for human nutrition. The nucleic acid of yeast is mainly ribonucleic acid or RNA, and in this application these terms will be used interchangeably.

In U.S. Pat. No. 3,887,431, a process is described whereby yeast protein concentrate containing a low level of ribonucleic acid (RNA) is produced by degradation of the yeast RNA by the ribonuclease of the yeast itself. This patent teaches that it is more desirable to extract the yeast protein from broken yeast cells under highly alkaline conditions than under lower pH conditions such as neutrality.

It is well known that various metal ions are required for the activation or stabilization of various enzymes. However, it has not been known until this discovery that the presence of zinc salts or biologically available zinc at certain critical concentrations stabilizes yeast ribonuclease against the effect of alkaline conditions, that is, a pH of greater than about 7. The zinc is required to assure that the nucleic acid accompanying the protein is degraded by the yeast ribonuclease to nucleosides and nucleotides. Zinc salts or biologically available zinc may be added to the yeast growth broth or at any of several operational points in the process used to prepare a yeast protein concentrate having a low nucleic acid content.

Yeast growth processes are known (U.S. Pat. No. 3,616,249) which use high levels of zinc compounds to optimize yeast yield when the yeasts are grown on hydrocarbons. However, the yeast growth processes of the present invention do not require the addition of high levels of zinc compounds to achieve satisfactory yeast yields.

When food yeasts are grown on molasses, beer wort, or cheese whey, there is sufficient zinc native to the substrate itself to provide for an optimal yield of yeast. Such yeasts do not have sufficient zinc content to protect the ribonuclease of the yeast against degradation by alkali when the yeast cells are ruptured and the protein extracted under highly alkaline conditions.

SUMMARY OF THE INVENTION

The invention comprises a method of making yeast protein of low nucleic acid content wherein zinc salts are added at certain critical points in the process to activate endogenous nuclease which depolymerizes the nucleic acid.

DETAILED DESCRIPTION

There has been developed a process to selectively extract, activate and utilize the endogenous ribonuclease present in microbial cells. It has been discovered that the extraction of a homogenate of yeast cells at an alkaline pH causes ribonuclease to be present in the soluble cytoplasmic materials, but that the addition of zinc salts to the yeast growth broth, or at other points in the process for making yeast protein isolate before raising the pH to a highly alkaline condition, allows the ribonuclease to degrade the ribonucleic acid of the yeast protein to an extremely low level.

Several advantages of this process are readily apparent. One advantage is that the nucleic acid content of the isolated protein is significantly reduced. Another advantage is that extraction can be carried out at higher alkalinity. Extraction is preferred at pH 9.5 because this is the pH level at which the greatest amount of nuclease is solubilized and available for subsequent reduction of nucleic acid in the protein isolate.

Yeast cells (biomass) is produced by methods known to those versed in the art. The main considerations are that the yeast be of food grade and produced in good yield. Biomass of *Saccharomyces cerevisiae, Saccharomyces carlsbergensis, Kluyveromyces fragilis* and *Candida utilis* have been utilized.

The biomass is grown in a conventional manner, harvested by centrifugation or filtration and water washed. The biomass is then ruptured by any of several known methods, such as high pressure homogenization. The main consideration is to rupture the majority of cells under such conditions that the majority of protein remains in the soluble state, and can be harvested in a later step. The presently preferred method is homogenization under the following conditions:

Pressure — 5000–15000 psig.
Passes through Homogenizer — 1 to 5
Temperature — 32°–122° F.
pH — 4.5–6.5

In the process, the homogenate is adjusted to a pH of above 5.5, preferably between 9.0 to 9.5, with alkali to maximize protein solubility. The homogenate is then separated by centrifugation into a cell wall residue and an extract, usually referred to as the alkaline extract. The protein in the alkaline extract contains between 10 and 13 percent nucleic acid. If the protein is recovered by precipitation of the alkaline extract by acidification, the accompanying nucleic acid will remain at this level in the protein aggregate which is too high for most uses in human feeding.

It has been found that addition of zinc at certain points in the aforedescribed process will activate or protect the endogenous nuclease of the yeast, so that it will degrade the nucleic acid to a level tolerable for human consumption of the protein.

If zinc is added to the growing yeast, or to the yeast cells prior to homogenization, or to the homogenate of cell walls and yeast protein before it is made highly alkaline, the endogenous nuclease of the yeast will be protected during the step of high alkalinity and will subsequently be available to degrade the yeast nucleic acid to a tolerable level.

One means of subsequently activating the nuclease in the alkaline protein extract is to adjust the pH from 9.5 to about 6.0 at a temperature of 50°-60° C., and then allow this system to incubate for about 2 hours under these conditions. Under these conditions the RNA of the alkaline protein extract decreases markedly to its constituent nucleosides and nucleotides. These are separated from the protein when the protein isolate is precipitated from the alkaline extract by acidification. The nucleic acid constituents remain in the solubles fraction which remains after acidification.

Factors that affect the degree of activation or stabilization of yeast nuclease by means of the zinc addition process are:
(1) the point in the process at which the zinc is added,
(2) the concentration of zinc added to the yeast protein,
(3) the pH of the protein extract medium.

These factors can interact to affect the protein composition and amount of nucleic acid in the yeast protein isolate. The discussion which follows will describe the interaction of these factors.

EFFECT OF THE POINT OF ADDITION OF ZINC

If zinc, either in salt form or in bioavailable form, is added to the yeast growth broth, the resulting protein isolate is characterized by a reduced level of nucleic acid (see Examples 1 and 2).

If zinc is added to the yeast cells either before homogenization or to the homogenate prior to the adjustment to pH 9.5, i.e., before the pH has been raised above about 7, the resulting protein isolate incurs a marked reduction in the nucleic acid level. However, if zinc is added to the protein extract at pH 9.5 or at any time subsequent to the pH being raised above about 7, the resulting protein isolate does not realize a significant reduction in nucleic acid after nuclease activation (see Example 5).

EFFECT OF CONCENTRATION OF ZINC

If zinc is added to the yeast growth broth in increasing concentrations (mg. Zn/gal. growth broth), it becomes evident that the reduction in nucleic acid of the protein isolate is in direct relation to the amount of zinc added (see Example 4).

If zinc is added to the whole yeast cell slurry before homogenization in increasing concentrations (mg. Zn/g. yeast cells), it can be seen that the nucleic acid content of the protein isolate is reduced until the zinc concentration reaches the optimum level (see Example 6), at which point, the addition of higher concentrations of zinc will adversely affect the protein isolate.

When zinc is added to the yeast growth broth medium, from about 15 to about 60 mg. Zn/gal. growth broth can be used, preferably from about 18 to about 40 mg. Zn/gal. broth.

When zinc is added to the whole cell slurry or to the homogenate, from about 0.05 to about 0.6 mg. Zn/g. yeast cells, preferably from about 0.2 to about 0.24 mg. Zn/gm. yeast cells, on a dry basis is used.

EFFECT OF pH OF EXTRACT MEDIUM

If no zinc is introduced into the yeast cell solution before homogenization, nucleic acid is degraded to a greater degree by activated ribonuclease in a protein extract of neutral pH than in such an extract with a more alkaline pH. However, if zinc is added to the yeast cell solution before homogenization at substantially a neutral pH, nucleic acid is degraded to a greater degree by ribonuclease when the protein solution subsequently is made alkaline rather than when it remains neutral. This phenomenon holds true until an optimum zinc concentration is attained (see Example 6).

It has been further found that the role of zinc is unique among heavy metals with regard to activation of endogenous ribonuclease of yeast cells (see Example 3).

Following are detailed examples of this invention.

EXAMPLE I

A commercial cultivation of baker's yeast was carried out using 1000 lbs. of seed yeast. To this seed yeast was delivered in a logarithmically increasing fashion 12,000 lbs. of sugar in the form of 22,460 lbs. of molasses. The cultivation was fortified with 307 gallons aqueous ammonia (28% $NH_3$) and 20.5 gallons of 75% phosphoric acid. These adjuncts were added proportionately to the molasses. The phosphoric acid solution contained such an amount of $ZnSO_4 \cdot 7 H_2O$ as to provide about 35 mg. Zn per gallon of fermenting broth. The cultivation endured 12.25 hours producing a net yield of 5450 lbs. of yeast. After harvesting, washing, and rupturing the cells, an alkaline extract was prepared and the protein extract was allowed to incubate at pH 6.0 for 2 hours at 60° C. The resulting protein concentrate contained 1.9% RNA. The yeast contained 438 $\mu$g Zn per g. dry substance.

EXAMPLE 2

Yeast was grown in a manner identical to that in Example 1 with the exception that no source of zinc in excess of that native to the molasses was added to the growing yeast. The resulting protein concentrate contained 3.7% RNA. The protein contained 141 $\mu$g Zn per g. dry substance.

EXAMPLE 3

*Saccharomyces cerevisiae* was grown on a mixture of beet and cane molasses. Nitrogen and phosphorous were supplied as a mixture of ammonium-hydroxide, ammonium sulfate and phosphoric acid. Several otherwise identical fermentations were supplied with a single different metallic salt each at the rate of 60 mg. equivalent of the metallic moiety of the salt per gallon of fermentation broth during the growth period. The cultivations were carried out otherwise identically and in the manner used to produce baker's yeast. The cells of each cultivation were harvested, concentrated and homogenized at 9000 psi in a Manton Gaulin homogenizer. The pH of the homogenate was adjusted to 9.5 with alkali and the protein dissolved. The cell walls were removed by centrifugation. The reaction of the dissolved protein was adjusted to pH 6.0 with HCl and the acidified system held for 2 hours at 60° C. Table I shows that only the cultivation supplied with zinc possessed an active nuclease which markedly degraded the RNA.

TABLE I

| Metal Added | RNA Content of Yeast Protein (%) | |
|---|---|---|
| | Before Activation of Nuclease | After Activation of Nuclease |
| None | 9.51 | 7.61 |
| Zinc | 10.60 | 1.95 |
| Magnesium | 10.85 | 7.87 |
| Manganese | 11.06 | 8.50 |
| Iron | 9.99 | 6.89 |
| Aluminum | 10.47 | 8.02 |
| Calcium | 10.72 | 7.77 |
| Cobalt | 11.90 | 6.61 |

The dependence of the extent of RNA degradation by the yeast endogenous nuclease upon the quantity of zinc supplied to the growing yeast is shown in Example 4.

EXAMPLE 4

Baker's yeast (Saccharomyces cerevisiae) was grown in a manner familiar to those skilled in the art using a mixture of beet and cane molasses. Nitrogen and phosphorous were supplied in the form of ammonium hydroxide and phosphoric acid. During the course of cultivation zinc as $ZnSO \cdot 7 H_2O$ was added to the growth broth in a series of cultivations at increasing levels as shown in Table II.

TABLE II

| (1) Zn as $ZNSO_4 \cdot 7 H_2O$ Added per gallon Growth Broth (mg.) | (2) Zinc Content of Yeast Grown (µg/g) | (3) Zinc Content of Yeast Protein Isolate (µg/g) | (4) % RNA in Yeast Protein Isolate After Ribonuclease Activation |
|---|---|---|---|
| 0 | 88 | 122 | 7.10 |
| 9 | 170 | 369 | 5.77 |
| 18 | 239 | 531 | 1.99 |
| 28 | 274 | 578 | 1.78 |
| 35 | 353 | 727 | 1.33 |
| 49 | 490 | 978 | 1.28 |

It should be noted that where no zinc was added, the yeast possessed a zinc content which is a reflection of the native zinc contained in the molasses (Column 1). As the amount of zinc added per gallon of growth broth was increased, there was an increase in the amount of zinc absorbed by the growing yeast cells (Column 2) and contained in the several protein isolates made from these cell crops (Column 3). After alkaline extraction of RNA-containing protein isolate from the cell crops which had been harvested, washed, and mechanically ruptured, the ribonuclease of the yeast was allowed to digest the RNA. This was accomplished by incubating the RNA-rich protein isolate at 60° C. for 2 hours at pH 6.0. This caused a reduction in the RNA contents of the protein isolates (Column 4) in direct relationship to the amounts of inorganic zinc added per gallon of yeast growth broth (Column 1) and in direct relationship to the contents of zinc in the yeast cell crop (Column 2) and the yeast protein isolates (Column 3). It is shown that the level of RNA in the final protein isolate is a function of the amount of zinc available to the growing cell.

In order that the RNA content be reduced to about two percent or less of the protein isolate, zinc had to be added at a level of at least 18 mg. per gallon of growth broth and had to be maintained at a level of at least 240 micrograms per g. d.s. of the yeast cell crop.

Zinc may be added to the protein concentration process at various points after cell growth to activate or protect the endogenous nuclease which degrades the RNA of the soluble yeast protein. This is shown in Example 5, Table III.

EXAMPLE 5

The amount of Zn as $ZnSO \cdot 7 H_2O$ was sufficient to provide about 300 ppm Zn on the yeast dry solids basis to produce a protein concentrate about 700 ppm Zn on a dry solids basis. The nuclease was activated by passing the pH 6.0 protein extract through a coil at 60° C. The reaction time was about 5 minutes.

TABLE III

| Point of Zinc Addition | % RNA in Protein Concentrate Before Nuclease Activation | % RNA In Protein Concentrate After Nuclease Activation |
|---|---|---|
| To Growth Medium (pH 4.5-6) | 11.06 | 3.18 |
| No Zinc Added (Control) | 10.21 | 8.16 |
| To Yeast Before Homogenizaton (pH 5-6) | 10.21 | 4.00 |
| To Homogenate (at pH 5-6) Before adjusting to pH 9.5 | 10.21 | 4.65 |
| To Protein Extract at pH 9.5 | 10.21 | 7.83 |
| To Protein Extract After Readjustment to pH 6.0 from pH 9.5 | 10.21 | 8.25 |

It is again evident that addition of Zn to the growth medium activates the nuclease. Likewise, the enzyme may be activated at any point until the homogenate is made alkaline.

EXAMPLE 6

Not only is the presence of zinc unique in protecting the yeast ribonuclease from alkaline degradation but the amount of zinc available to the post growth operation is critical to the reduction of the yeast RNA. In this example, yeast was grown without any added zinc; the yeast contained only the zinc available from its molasses growth medium, 92 µg zinc per g. dry solids yeast. Increasing levels of zinc were added to the whole yeast cell slurry before homogenization. The yeast cells were then homogenized and each cell slurry containing a specific amount of zinc was divided into two parts. One part was adjusted to pH 7.0 and the other part was adjusted to pH 9.5 for protein extraction. The cell walls of every part were centrifuged away and the ribonuclease of every part was activated in the manner cited previously. Table IV shows that there is an optimum level of added zinc to produce maximum reduction of RNA by the ribonuclease. It also shows that protein extraction at pH 9.5 produces a lower RNA content protein concentrate than does extraction at pH 7.0.

TABLE IV

| Zinc Added To Yeast Cells Before Homogenizaton (µg/g) | pH of Protein Extraction | % RNA After Ribonuclease Activation | Zinc Content of Protein Concentrates (µg/g) |
|---|---|---|---|
| 0 | 7.0 | 8.18 | 180 |
| 0 | 9.5 | 13.24 | 186 |
| 50 | 7.0 | 9.13 | 275 |
| 50 | 9.5 | 7.21 | 257 |
| 100 | 7.0 | 9.45 | 443 |

TABLE IV-continued

| Zinc Added To Yeast Cells Before Homogenizaton (μg/g) | pH of Protein Extraction | % RNA After Ribonuclease Activation | Zinc Content of Protein Concentrates (μg/g) |
|---|---|---|---|
| 100 | 9.5 | 5.99 | 414 |
| 150 | 7.0 | 6.76 | 550 |
| 150 | 9.5 | 2.79 | 572 |
| 200 | 7.0 | 7.12 | 660 |
| 200 | 9.5 | 3.15 | 650 |

It is to be noted that where no zinc is added to the cells prior to rupture the amount of native zinc was insufficient to protect the ribonuclease when the extraction pH was 9.5. In this case the less severe damage to the ribonuclease where the cells slurry was at pH 7.0 permitted a greater degree of RNA degradation as reflected in the relatively lower RNA content (8.18%) than in the highly alkanline pH 9.5 protein solution (RNA content 13.24%). However, as increasing levels of zinc are added, it is definitely advantageous to extract the yeast protein from the ruptured cells at the higher pH. As the concentration of added zinc is increased, the activity of the ribonuclease also increases; that is, a lower RNA content is realized when the yeast protein has been solubilized at the higher pH. This means that added zinc protects the ribonuclease enzyme as its milieu becomes more alkaline and that the more alkaline solubilization of the yeast protein also provides for a greater amount of ribonuclease solubization or availability for the subsequent step of reducing the RNA content of the yeast protein through the action of the ribonuclease enzyme.

EXAMPLE 7

There is also an optimal concentration of zinc to be added to the homogenized yeast cells before preparing the alkaline protein extract. The same batch of yeast used in Example 6 whichwas grown without added zinc was homogenized and various levels of Zn as $ZnSO_4 \cdot 7H_2O$ were added to this homogenate. The homogenate was then made alkaline to solubilize the protein, and the cell walls were centrifuged away. The soluble protein was subjected to nuclease action as described in the proceding Examples. Table V shows that the reduction in RNA achieves an optimum at about 150 μg Zn per g. dry yeast homogenate equivalence.

TABLE V

| Zinc Added To Yeast Cell Homogenate (μg/g) | % Yest Protein RNA Before Nuclease Activation | After Nuclease Activation | Zinc Content of Yeast Protein Concentrate (μg/g) |
|---|---|---|---|
| 50 | 13.0 | 7.41 | 271 |
| 100 | 13.0 | 6.47 | 398 |
| 150 | 13.0 | 2.00 | 543 |
| 200 | 13.0 | 3.72 | 654 |

EXAMPLE 8

*Candida utilis* was grown in a customary manner on a mixture of beet and cane molasses. Nitrogen was supplied as ammonium hydroxide and phosphorous as phosphoric acid. Zinc was supplied in the following amounts to the usual cultivations to show the dependence of active endogenous ribonuclease upon the level of zinc supplied beyond that native to the substrate (Table VI).

TABLE VI

| Cultivation | Zn Added per Gallon Fermentor Broth (mg) | Zn Content of Harvested Yeast (μg/g) |
|---|---|---|
| 1 | 0 | 58 |
| 2 | 7.36 | 123 |
| 3 | 14.7 | 175 |
| 4 | 29.5 | 228 |

The harvested yeast was washed, concentrated and mechanically disrupted to free the proteins. The homogenate was adjusted to pH 9.2 and the protein solubilized and the cell walls centrifuged away. The protein solution was adjusted to pH 6.0 and heated at 60° C. by passing through a heated coil. Table VII shows the effect of the addition of zinc upon the degradation of RNA in protein concentrate derived from *Candida utilis*.

TABLE VII

| Yeast From Cultivation | % Total RNA Before Activation Of Endogenous Nuclease | % Total RNA After Activation Of Endogenous Nuclease | Zinc Content of Protein Concentrate After Activation of Endogenous Nuclease (μg/g) |
|---|---|---|---|
| 1 | 8.32 | 5.22 | 133 |
| 2 | 7.71 | 2.51 | 292 |
| 3 | 7.57 | 1.61 | 357 |
| 4 | 7.88 | 1.54 | 477 |

It is evident that supplying zinc to the growing *Candida utilis* permitted the degradation of the yeast nucleic acid in proportion to the level of zinc supplied.

What is claimed is:

1. A process for the activation, protection, and stabilization of the endogenous ribonuclease of yeast against alkaline conditions which comprises adding zinc salts or biologically available zinc to a yeast medium used in the production of a protein concentrate having a reduced nucleic acid content before the pH of the yeast medium is raised above about 7.

2. A process according to claim 1 whereby the zinc salts or biologically available zinc is added to the yeast growth broth at a concentration of from about 15 mg. to about 60 mg. of zinc per gallon of growth broth.

3. A process according to claim 1 wherein the yeast is harvested and washed and the zinc salts or biologically available zinc is added to the harvested and washed yeast at a concentration of about 50 to about 600 micrograms of zinc per g. of yeast solids on a dry basis in order to stabilize the ribonuclease against subsequent alkaline conditions when the yeast protein is solubilized.

4. A process according to claim 1 wherein the yeast is harvested, washed and ruptured and wherein the zinc salts or biologically available zinc is added to the harvested, washed and ruptured yeast at a concentration of between 50 and 600 micrograms of zinc per g. of yeast solids on a dry basis in order to stabilize the ribonuclease against subsequent alkaline conditions when the yeast protein is solubilized.

5. A process according to claim 1 in which the yeast is selected from the group consisting of *Saccharomyces cerevisiae*, *Saccharomyces carlsbergensis*, *Kluyveromyces fragilis*, and *Candida utilis*.

6. A process according to claim 1 in which the zinc salt employed is selected from the group consisting of zinc sulfate, zinc chloride, zinc citrate, and zinc tartrate.

7. In a process for making yeast protein of reduced nucleic acid content wherein the yeast medium is raised to a pH of above about 8.5, the improvement which comprises adding zinc salts or biologically active zinc to the yeast medium prior to raising the pH of the yeast medium to above about 7, the zinc being added in an amount effective to protect the endogenous nuclease of the yeast against the normal deactivating effect of high pH so that the nuclease is available to depolymerize nucleic acid from protein without the zinc adversely affecting the protein.

* * * * *